(12) United States Patent
Ray

(10) Patent No.: US 6,458,131 B1
(45) Date of Patent: *Oct. 1, 2002

(54) APPARATUS AND METHOD FOR REDUCING SPINAL DEFORMITY

(75) Inventor: R. Charles Ray, University Place, WA (US)

(73) Assignee: Salut, Ltd., University Place, WA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/633,480

(22) Filed: Aug. 7, 2000

(51) Int. Cl.$^7$ ............................................... A61B 17/58
(52) U.S. Cl. .......................................... 606/61; 606/70
(58) Field of Search ............................... 606/61, 70, 71; 623/17.11, 17.15; 403/DIG. 9, 345, 346; 24/522; 269/89, 216, 218, 219

(56) References Cited

U.S. PATENT DOCUMENTS

| | | |
|---|---|---|
| 4,611,581 A | 9/1986 | Steffee |
| 4,648,388 A | 3/1987 | Steffee |
| 4,653,481 A | 3/1987 | Howland et al. |
| 4,655,199 A | 4/1987 | Steffee |
| 4,696,290 A | 9/1987 | Steffee |
| 4,719,905 A | 1/1988 | Steffee |
| 4,771,767 A | 9/1988 | Steffee |
| 5,000,166 A | 3/1991 | Karpf |
| 5,030,220 A | 7/1991 | Howland |
| 5,127,912 A | 7/1992 | Ray et al. |
| 5,281,223 A | 1/1994 | Ray |
| 5,300,073 A | 4/1994 | Ray et al. |
| 5,380,323 A | 1/1995 | Howland |
| 5,385,565 A | 1/1995 | Ray |
| 5,437,669 A | 8/1995 | Yuan et al. |

(List continued on next page.)

FOREIGN PATENT DOCUMENTS

| | | |
|---|---|---|
| EP | 0 564 046 A1 | 10/1993 |
| WO | WO 95/10240 | 4/1995 |

OTHER PUBLICATIONS

Advanced Spine Fixation Systems, Inc.: *Varigrip System*; brochure published in the United States, at least as of September 1, 2000.

*Primary Examiner*—David O. Reip
*Assistant Examiner*—Julian W. Woo
(74) *Attorney, Agent, or Firm*—Christensen O'Connor Johnson Kindness PLLC (57) ABSTRACT

An apparatus and method for the treatment of abnormal spinal curvature, such as, scoliosis, is disclosed. The apparatus includes a plurality of clamp sets and a single rail. The clamp set for affixing to a vertebra has a transverse plate having a center region and a first and a second end. The first end has a first pedicle extension, and the second end has a second pedicle extension. At least one pedicle extension is used to transmit a downward force during rotation of the vertebra. The clamp set also includes a first laminar hook located on the first end of the plate and is integral with the plate to hook on a superior portion of a first lamina of a vertebra. The clamp set also includes a second laminar hook to hook from an opposite direction on an inferior portion of a second lamina of the vertebra. The second hook is adjustable to allow clamping and unclamping of the clamp set. The clamp set includes a rail coupling member having a slot to receive a rail. The rail coupling member is located on the center region of the plate, and the slot is configured to accept the rail cross-sectional shape. A plurality of the clamp sets are attached along a portion of the spine, followed by adjustment and fixation of the individual clamp sets prior to attaching a rail. The rail is inserted into the slots of each clamp set to hold the clamp sets in the reduced form and in relation to one another. In one instance, the rail may have a plurality of sides.

23 Claims, 7 Drawing Sheets

U.S. PATENT DOCUMENTS

| | | |
|---|---|---|
| 5,437,673 A | 8/1995 | Alleyne |
| 5,470,333 A | 11/1995 | Ray |
| 5,527,312 A | 6/1996 | Ray |
| 5,531,745 A | 7/1996 | Ray |
| 5,531,747 A | 7/1996 | Ray |
| 5,582,612 A | 12/1996 | Lin |
| 5,688,273 A | 11/1997 | Errico et al. |
| 5,688,274 A | 11/1997 | Errico et al. |
| 5,690,629 A | 11/1997 | Asher et al. |
| 5,702,392 A | 12/1997 | Wu et al. |
| 5,733,284 A | 3/1998 | Martin |
| 5,928,232 A * | 7/1999 | Howland et al. .............. 606/61 |

\* cited by examiner

APPARATUS AND METHOD FOR REDUCING SPINAL DEFORMITY

FIELD OF THE INVENTION

The present invention pertains to apparatus and methods for realigning any abnormal curvature of the spine and more particularly to posterior instrumentation having claw-like clamp sets to affix to vertebrae which enable reduction of the vertebrae followed by attachment to a precontoured rail to reduce spinal deformities such as scoliosis.

BACKGROUND OF THE INVENTION

A normal spine when viewed from an anterior or posterior perspective is longitudinally aligned with a straight vertical line. The spine when viewed from either side presents a series of curvatures. The top curve in the neck or cervical spine has a convexity pointing anterior or towards the front. This type of curve (convexity pointing anterior) is called a lordotic curve. The next lower curve in the chest area or thoracic spine has a convexity pointing posterior or towards the back. This type of curve (convexity pointing posterior) is called a kyphotic curve. The lowest curve in the low back or lumbar area again has a convexity pointing anteriorly.

Scoliosis is a deformity of the spinal column with three components. The first is an apparent side bending of the spine when viewed from the front or back (anterior/posterior or AP view). This is a coronal plane deformity. The second component is a loss of the normal kyphotic curvature in the thoracic or chest area when viewed from the side. This is a sagittal plane deformity. The third component is the rotation of the spine around its own long axis. This is an axial plane deformity. This latter deformity can be appreciated on either a cross sectional x-ray study such as a CT scan (computerized axial tomography scan) or more importantly from the effect on the attached ribs. It is this rotation that causes the characteristic "rib hump" which is the most disturbing element of the deformity to the patient and the aspect of the deformity that is least well treated by current surgical treatment methods. Depending on the etiology of the spinal deformity, one or more instances of abnormal curvature may be present in the scoliotic spine and depending on the gravity of the deformity, the preferred treatment may involve surgical procedures. In severe cases, bone fusion and instrumentation may be indicated. Instrumentation merely serves to hold the vertebrae in their correct alignment while the bone fusion heals. Thus, in order to be effective, instrumentation must be able to correct vertebral alignment deformities in both the coronal and sagittal planes as well as correct for rotational aberrations.

Several procedures are available which include the use of either anterior or posterior instrumentation. Anterior and posterior instrumentation have their specific uses in different cases with attendant advantages and disadvantages. Posterior instrumentation is usually recommended for a typical deformity seen in patients which is known as a right thoracic curvature. One benefit to posterior instrumentation is its relatively less invasive nature as compared with most anterior methods.

Generally, posterior instrumentation involved the use of two longitudinal rods secured to the spine by the use of multiple hooks, wires or sometimes screws and to each other with connecting plates. The standard method of spinal deformity reduction was to attach a pre-bent, pre-cut rod in the anticipated correction shape to the spine with a loose connection between the rod and hooks via several types of known connectors. The rod was then rotated inside the connectors into the improved position. The connectors were then locked connecting the hook securely to the rod. A second rod was attached to the spine in a similar way with little if any correction obtainable at that time. Two plates or cross connectors were then attached to link the two rods together into one effective unit.

This method had several disadvantages. First, this technique most effectively corrected the sagittal and coronal plane deformities but did little if anything for the axial deformity. Second, since each hook was attached to its own respective single vertebra, all corrective force was applied to the vertebra in one location increasing the chance of hook cutout through the lamina. Third, since the rod was rotated with a loose connection, there existed the possibility for the hook to dislodge from the lamina sometimes with catastrophic consequences for the patient's spinal cord. Fourth, since a scoliotic deformity is an axial rotation of a free body (the vertebra) without a fixed pivot, it requires two simultaneous forces in opposite directions around an axis (a torque) to correct it. This concept was addressed in an earlier patent concerning a two rod system. No current system provides this. Fifth, a two rod system leaves the rods in a lateral position where the paraspinal muscles are suppose to attach to the bone to help heal the spinal fusion. Sixth, since the rod is pre-bent and pre-cut to length before the correction is obtained and the rigidity of the patient's spine is variable and hard to measure preoperatively, the ultimate length and shape are determined from an educated guess.

In view of the short comings of the existing procedures for treating scoliotic spines, there is a need for improvements which allow the use of a single-rod system that will reduce the scoliotic spine in all three planes, distribute the force during reduction over the vertebra, will attach rigidly to the spine before the reduction maneuver, will apply a true derotation torque to correct the axial plane deformity, will leave the longitudinal rod in a more biologically advantageous central place (where the spinous process was), and allow reduction of the deformity before cutting and contouring the rod.

SUMMARY OF THE INVENTION

The present invention relates to an apparatus and method for reducing a scoliotic spine. The apparatus includes at least one vertebral clamp set having a plurality of laminar hooks and a coupling member for receiving a single central rail. The rail is cut and contoured to a corrected alignment of the spine so that it can be attached to one or more clamp sets after reduction of the spine has been performed.

A preferred embodiment of the present invention includes four clamp sets and a single rail, each clamp set has a transverse plate with a center region, and a first and second end. The first end has a pedicle extension to transmit force to a pedicle of a vertebra during reduction and the second end also has a pedicle extension to transmit force to a pedicle during reduction of the vertebra when the force is applied in the opposite direction. The plate has a first laminar hook to hook on a superior portion of a first lamina of a vertebra. The first hook is located on the first end of the plate and is integral with the plate. The plate has a second laminar hook to hook on an inferior portion of a second lamina of a vertebra, such that the first and second hook are in opposed configuration, giving a claw-like hold on the vertebra. The second hook is located on the second end of the plate and is made adjustable with the plate to facilitate clamping and unclamping. The plate also includes a rail coupling member having a slot to receive a precontoured rail. The slot surface is configured to engage the rail cross-sectional area and shape. The rail will preferably be multisided having between 16 to 24 sides, and possibly as little as 4 to as many as 120.

In another embodiment of the present invention, a clamp set for reducing spinal deformity is disclosed. The clamp set for affixing to a vertebra has a transverse plate having a center region and a first and a second end. The first end has a first pedicle extension, and the second end has a second pedicle extension. At least one pedicle extension is used to transmit a downward force during reduction of the vertebra. The clamp set also includes a first laminar hook located on the first end of the plate and is integral with the plate to hook on a superior portion of a first lamina of a vertebra. The clamp set also includes a second laminar hook to hook from an opposite direction on an inferior portion of a second lamina of the same vertebra. The second hook is adjustable to allow clamping and unclamping of the clamp set. The clamp set includes a rail coupling member having a slot to receive a rail. The rail coupling member is located on the center region of the plate, and the slot is configured to accept the rail cross-sectional area and shape.

In another embodiment of the present invention, a method for reducing the spine is disclosed. The method will include the steps of: attaching a plurality of vertebral clamp sets to vertebrae along the extent of the deformity of the spine, attaching reduction clamps to the vertebral clamps, attaching self-retaining arms to the reduction clamps in a loosened state, reducing the vertebra sequentially by grasping the reduction clamp and maneuvering it into an optimal position and the holding it there by securing the self retaining arm in a rigid condition, then once the optimum position has been obtained, cutting and contouring the rod to the reduced spine. The rail (rod) is then secured to the individual central connectors and the reduction clamps are removed.

Many advantages are obtained with the use of posterior instrumentation constructed in accordance with the present invention. One advantage of a single rail system over a double rod system is that a single rail causes less disruption of the healing muscles and allows more area for bone grafts. Another advantage is more secure instrumentation attached to the individual vertebra as compared with singular bone hooks which may shear from their lamina and cause damage to bone or nerve tissue. Another advantage is having a rail contoured to the spine after reduction has taken place which avoids incorrect rail length and over-compensation or under-compensation of the rail contours. Another advantage is the use of a clamp set with pedicle extensions which distribute rotational forces downward onto the pedicle rather than solely on the lamina during reduction of the vertebra, thus allowing greater rotational forces without fear of damaging bone tissue or popping hooks from their laminae. Another advantage is the use of a multi-sided rail which allows for fine adjustment of the degree of reduction without slippage between the clamp sets and the rail, and thus can eliminate the use of a two rod system and further provides greater rotational stability.

BREIF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention is directed to an apparatus and method for reducing the deformity of a scoliotic spine. The apparatus includes at least one vertebral clamp set having a plurality of laminar hooks for clamping to a vertebra and a coupling member for receiving a rail. The rail is attached to the coupling member after the vertebra has been reduced. Therefore, the rail is contoured to the corrected spinal curvature before placement on the instrumentation.

Figure 1:
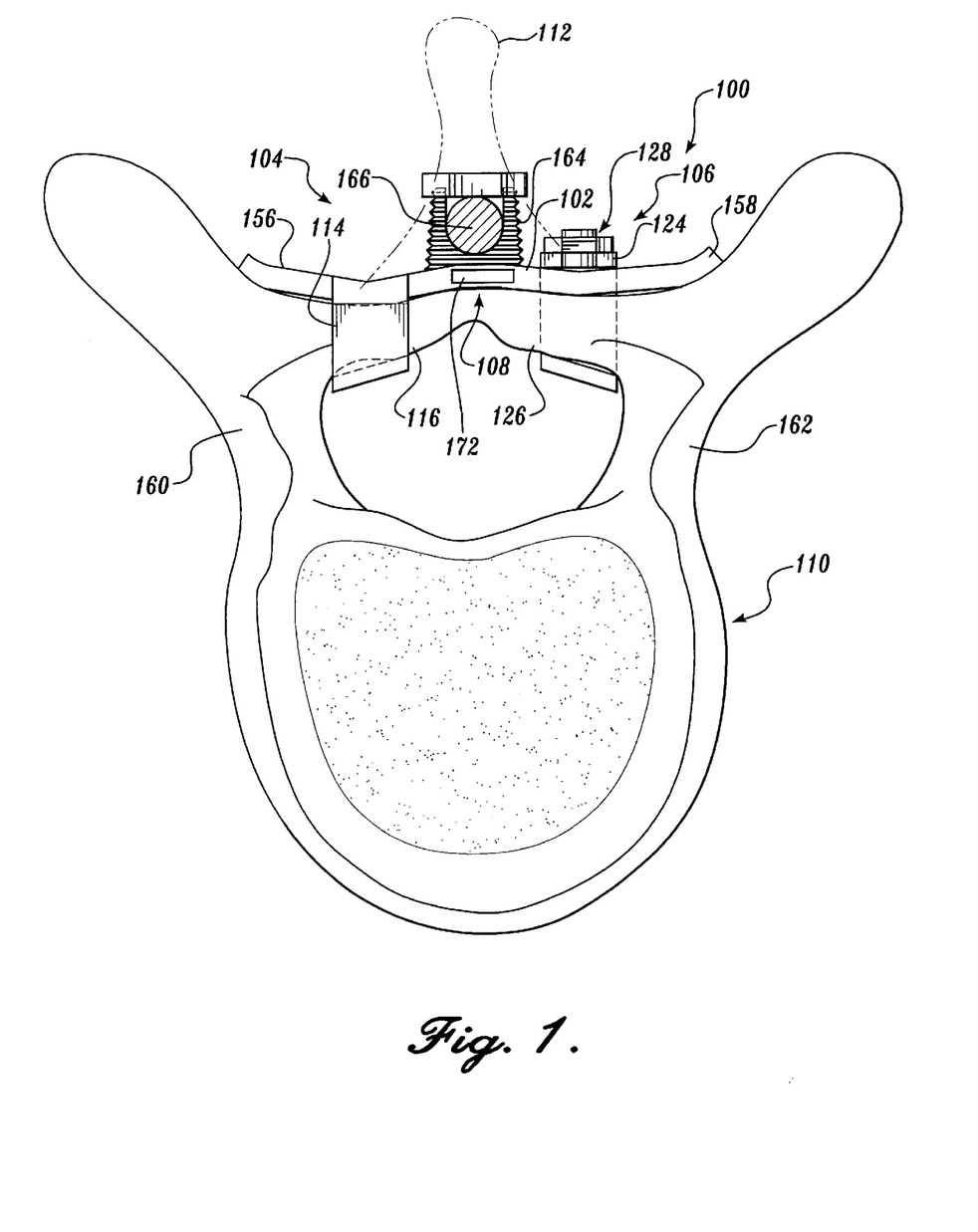
FIG. 1 shows a top plan view of an embodiment of a clamp set constructed in accordance with the present invention.

Referring to FIG. 1, a component of the apparatus for reducing scoliosis is a clamp set 100 having a transverse plate 102 with a first end 104, a second end 106, and a center region 108. In use, the transverse plate 100 lies posteriorly of the vertebra 110. First 104 and second 106 ends are located lateral of the spinous process 112 (shown in phantom), while the center region 108 lies near the center of the base of the spinous process 112 (shown in phantom). It should be understood that several anatomical parts of the vertebra may be removed to place the clamp set 100 in its proper position.

The transverse plate 102 will generally define a planar rectangular body. However, the transverse plate 102 may be contoured to match the contours of the particular vertebra 110 to which it is attached. For example, the embodiment of FIG. 1 shows a transverse plate 102 having angled surfaces along the length of the body to more closely approximate the contours of the posterior portion of vertebra 110. Located on the first end 104 of transverse plate 102 is a first hook 114. A hook may be defined as any angled piece having ends facing in substantially the same direction, so as to form a capture region on three sides and one open side. In use, the first hook 114 fits over a portion of a first lamina 116, with the open side pointing in either the superior or anterior position depending on the particular situation. As with transverse plate 102, first hook 114 may have angled surfaces to match the contours of the vertebra 110.

As shown in FIG. 1, first hook 114 is continuous or integral with transverse plate 102 and extending perpendicular to the long axis of transverse plate 102. Attachment of first hook 114 to the transverse plate 102 may also be performed in any number of mechanically expedient ways, such as bolting or welding the hook to the plate. Transverse plate 102 is in a posterior position in relation to the vertebra 110, so first hook 114 will proceed from transverse plate 102 in a superior direction (or inferior direction depending on the situation). First hook 114 will then proceed anteriorly to an anterior part of first lamina 116, and then proceed in an inferior direction so as to create a hook which hooks onto the first lamina 116 from the superior direction on three sides, the transverse plate 102 forming part of a side.

While one alternate embodiment of a hook has been described, it should be readily apparent that hooks may take any number of forms, including arcuate, or cylindrical shapes or any combination thereof. While in one alternate embodiment, an integral hook is described, it should be readily apparent that hooks which are attached by other methods are also contemplated. For instance, a hook may be welded onto the plate or held by attachment devices, such as bolts or screws.

Referring again to FIG. 1, a second hook 124 is located on the second end 106 of the transverse plate 102 and extends perpendicular to the long axis of the plate 102. Second hook 102 is configured opposite of the first hook 114, so as to hook on a second lamina 126 of the same vertebra 110 from an inferior direction. In the embodiment of FIG. 1, second hook 124 is attached to transverse plate 102 by the use of an adjustable device 128. Preferably, at least one hook is made adjustable or even detachable. Since first 114 and second 124 hook are in opposing or claw-like configuration, adjustability enables the attachment of the clamp set 100 to the vertebra 110 or allows its release. To enable the opposing claw-like holding action, second hook 124 will attach to the second lamina 126 from an opposite direction as the first hook 114. Second hook 124 will proceed from transverse plate 102 in an inferior direction to an inferior part of the lamina 126. Second hook 124 will then proceed anteriorly to the anterior part of the lamina 126, and then proceed in a superior direction so as to hook onto the second lamina 126 from the inferior direction on three sides with the transverse plate 102. As with first hook 114, second hook may have angled surfaces to match the contours of the vertebra 110.

Figure 3:
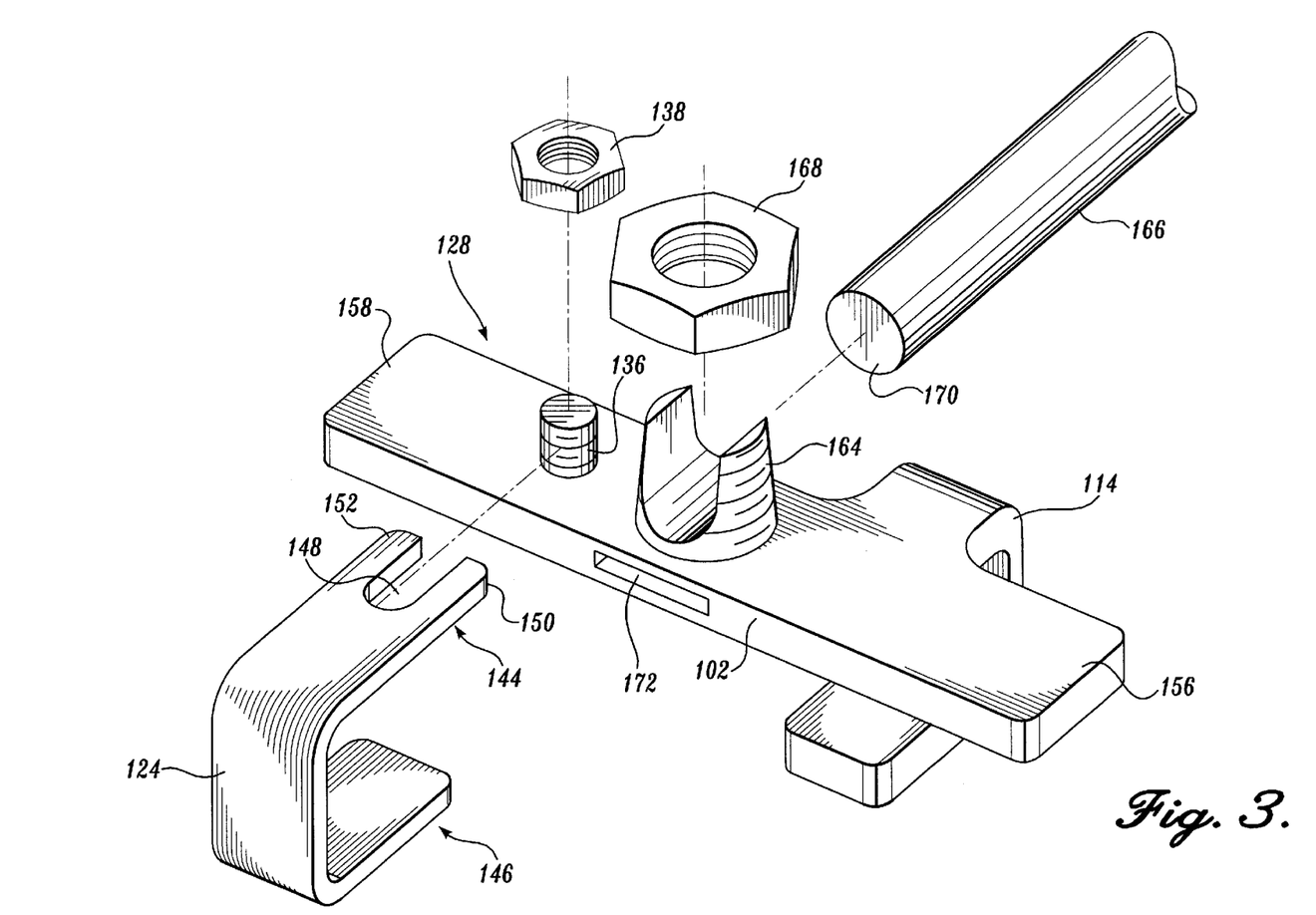
FIG. 3 shows a perspective exploded view of the clamp set of FIG. 1.

It is with reference to FIG. 3 that a description of the adjustable second hook 124 is next undertaken. It is intended that the alternate embodiment of FIG. 3 is meant to function in substantially the same manner as the embodiment of FIG. 1. Furthermore, FIG. 3 shows one of many alternates of FIG. 1 having modifications tailored for a particular vertebra. It should also be understood that each vertebra of a spinal column may be different, therefore necessitating modifications to each of the clamp sets in the whole of the instrumentation apparatus without detracting from the functionality as described in this specification.

Second hook 124 may be detachable from transverse plate 102 or may only be adjustable. Adjustability is minimally required to facilitate placement and removal of the clamp set 100. In the embodiment of FIG. 3, second hook 124 is made detachable, and includes an attachment member 128 for securing second hook 124 to transverse plate 102. Attachment member 128 is located on the second end 106 of the transverse plate 102 lateral of the center region and centered on the long axis of the plate 102. Attachment member 128 includes a bolt 136 projecting from transverse plate 102 in a posterior direction when clamp set 100 is in use. Bolt 136 has threads to engage corresponding nut 138. Nut 138 is used to snug the second hook 124 to the transverse plate 102 in the manner described below. Second hook 124 is a curved piece having two ends 144, 146 pointing substantially in the same direction. One end 144 will be positioned posteriorly in relation to the second end 146. On the posterior end 144, second hook 124 has a notch 148, sized and configured to fit into the bolt 136 as the second hook 124 is slid from the side or top of the bolt 136. Posterior end portion 144 of second hook 124 has first 150 and second 152 fingers that extend around bolt 136 and create a pressure surface for nut 138 to snug against from the exterior surfaces. The nut 138 keeps second hook 124 securely held to transverse plate 102 when in use. Although one embodiment has been described with respect to second hook 124 and second hook attachment member 128, other alternative embodiments of second hook 124 and attachment member 128 are possible. For example, the second hook may have an aperture rather than a notch to fit into the bolt. Further, it is possible for the bolt to reside on the hook and aperture or for the notch to reside on the transverse body.

Figure 7:
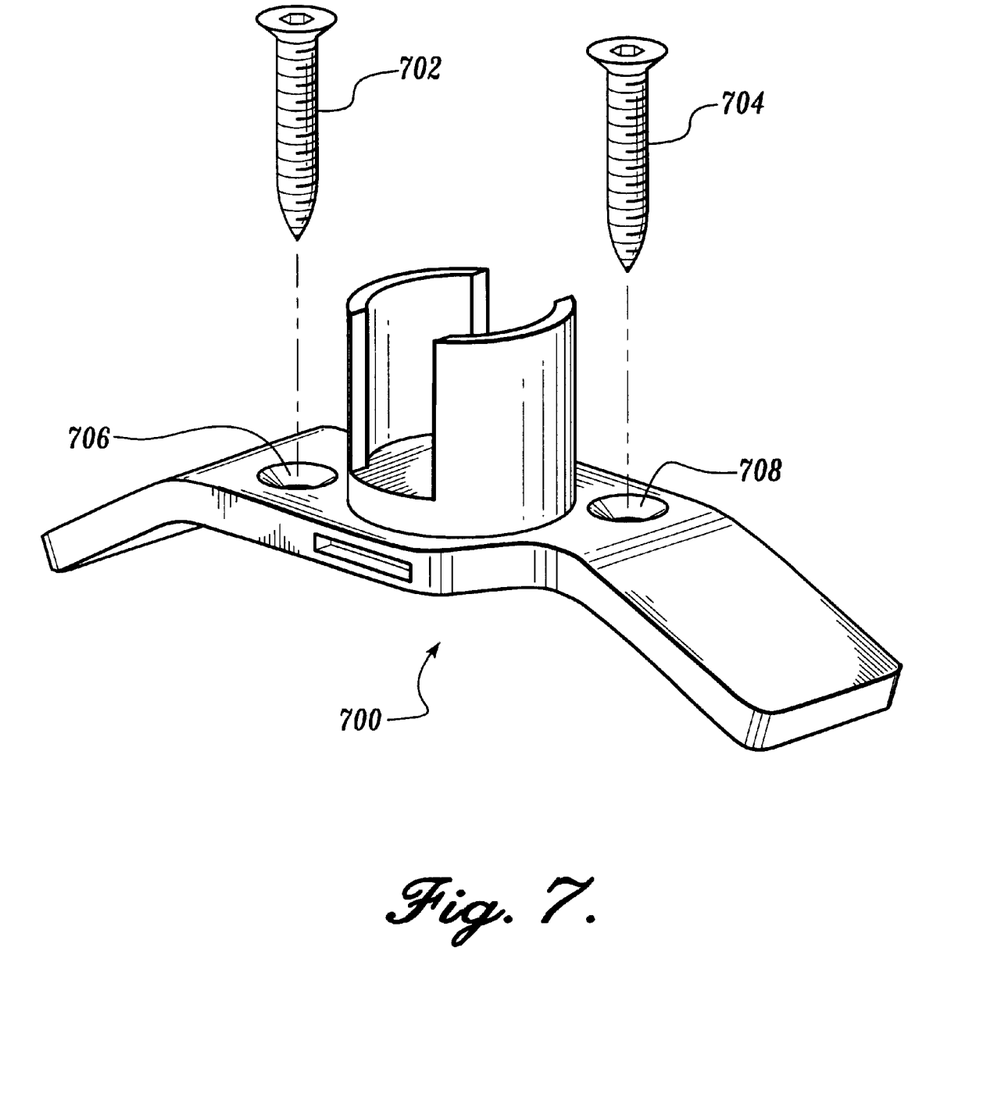
FIG. 7 shows a perspective view of an embodiment of a clamp set constructed in accordance with the present invention.

While first and second vertebral securement devices have been described as hooks, other vertebral securement devices may be employed. FIG. 7 shows an alternate of the vertebral securement devices. In the embodiment of FIG. 7, a plurality of pedicle screws may be used in cooperation with the clamp set of the present invention. The pedicle screws are described in the inventor's previous U.S. Pat. Nos. 5,470,333 and 5,127,912, which are herein incorporated by reference. FIG. 7 shows a clamp set 700, with a first pedicle screw 702 located on the first end 704 of the clamp set 700 and a second pedicle screw 706 likewise centrally located, but on the opposing second end 708 of the clamp set. The construction of the pedicle screws may take the form of any of the screws in the aforementioned patents. Located on first 704 and second 708 ends one is a countersunk bore 710 and 712, respectively, to accept rounded head pedicle screws 702 and 706. Countersunk bores and rounded heads provide for pivoting of pedicle screws about a central axis to accommodate varying vertebral anatomies.

Referring to FIG. 1, the clamp set 100 constructed in accordance with the present invention includes a first 156 and a second 158 pedicle extension formed so as to extend over a portion of a first 160 and second 162 pedicle on the same vertebra. First pedicle extension 156 is located on first end 104 of transverse plate 102 such that first pedicle extension 156 is continuous or integral with first end 104 of transverse plate 102. Pedicle extensions 156 and 158 function to transmit downward forces on the pedicle during rotation of the vertebra, therefore pedicle extensions are deemed to be that part of transverse plate ends 104, 106 which extend onto the pedicles of the vertebra. First pedicle extension 156 is lateral of the center portion 108 of the transverse plate 102. Transverse plate 102 includes a second pedicle extension 158 formed so as to extend over a portion of a second pedicle 162 of the same vertebra. Second pedicle extension 158 is located on second end 106 of transverse plate 102. Second pedicle extension 158 is continuous or integral with second end 106 of transverse plate 102. Second pedicle extension 158 is lateral of the center region 108 of the transverse plate 102 and opposite with respect to the first pedicle extension 156. As shown in the embodiment of FIG. 1, first 156 and second 158 pedicle extensions are slightly angled relative to transverse plate 102, however other alternates of this embodiment may have more or less angled surfaces or in some alternates be made to lie prone with no angled surfaces such as shown in FIG. 3. It should be apparent that pedicle extensions are formed so as to transmit downward forces onto pedicle during rotation, so in some alternates, the shape may take any of a number of configurations to conform to the particular pedicle. First 156 and second 158 pedicle extensions may also be shorter or longer depending on the features of the individual vertebra. While first 156 and second 158 pedicle extensions may be generally planar shaped pieces, first 156 and second 158 pedicle extensions may also be contoured to include curves to fit the anatomical features of the vertebra 110 and some anatomical features of the vertebra may be removed in order to position the first 156 and second 158 pedicle extensions over the first 160 and second 162 pedicles of the vertebra. While the embodiment of FIG. 3 may appear different, it should be readily apparent that the clamp set 100 of FIG. 3 is intended to function as the clamp set 100 of FIG. 1.

Referring to FIG. 1, the clamp set 100 constructed in accordance with the present invention includes a rail coupling member 164 located in the center region 108 of the transverse plate 102. In use, rail coupling member 164 will be positioned posteriorly with respect to vertebra 110. In the embodiment shown in FIG. 3, rail coupling member is a cylindrical threaded piece attached to the transverse plate 102 by any number of well-known methods, such as welding. The rail coupling member of FIG. 3 is intended to be similar to the coupling member of FIG. 1. While one embodiment of a rail coupling member has been described, other coupling members may have a horizontal slot or a nut which threads on the inside of the cylindrical body of the coupling member. Other coupling members may include two cylindrical bodies for attaching to two longitudinal rails, or a coupling member with two slots or recesses for more than one rail. Rail coupling member 164 is slotted to receive a longitudinal rail 166. Inside surface of rail coupling member 164 is configured to engage with a portion of the longitudinal rail 166 cross-sectional shape 170. Therefore, when cross-sectional shape 170 of rail 166 is circular, slot surface will assume a semi-circular shape to engage rail 166 on all but upper portion of rail 166. Rail coupling member 164 is threaded to engage a nut 168. Nut 168 can be snugged against upper portion of longitudinal rail 166 to keep rail 166 in position on the clamp set 100, thus preventing movement of the clamp set and vertebra in relation to rail 166. In the embodiment shown in FIG. 3, longitudinal rail 166 may have a circular cross-sectional shape 170, but other embodiments may have different cross-sectional areas and shapes.

Figure 4:
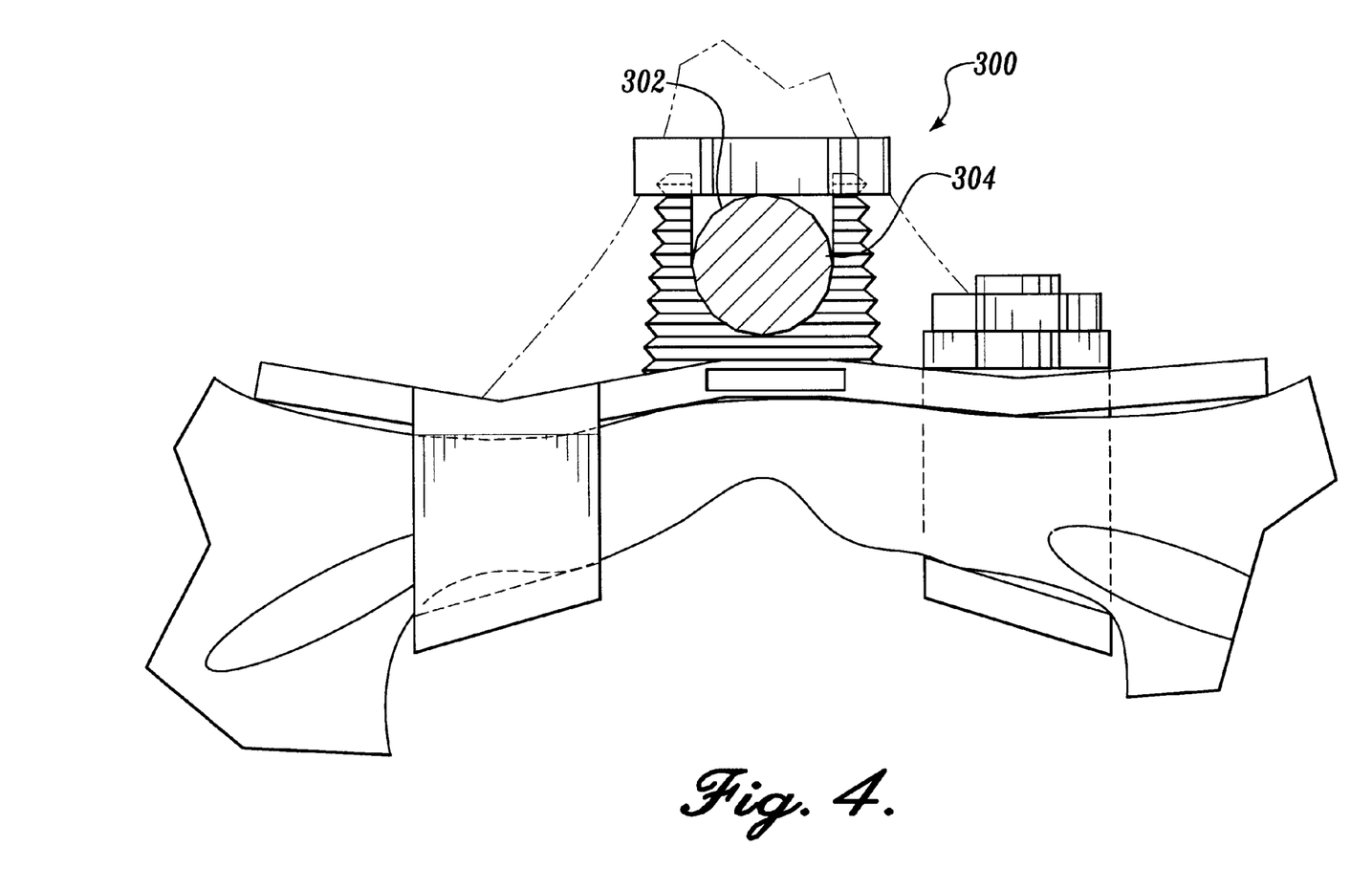
FIG. 4 shows an alternate embodiment for the clamp set of FIG. 1.

FIG. 4 shows the preferred embodiment of the clamp set 300 and longitudinal rail 302 constructed in accordance with the present invention. Particularly shown is the rail 302 having a multisided cross-sectional shape 304. The number of sides present in the cross-sectional shape may vary depending on the tolerance required in achieving the desired reduction of the spine. The cross-sectional shape may have as little as 4 sides and as many as 120 sides, and most preferably, 16 to 24 sides. It should be readily apparent that this embodiment of the clamp set is intended to function in substantially the same manner as the embodiments described by FIGS. 1, 2 and 3, except for use of the multi-sided rail.

When a multi-sided rail is used in cooperation with the clamp set of the present invention, the rail attachment member walls are slightly angled outward to give a narrowing taper to the channel created therein. In this manner, the rail may be rotated within the channel, but when the nut is snugged against the rail, the nut presses the rail into the narrower section of the channel and the rail is prevented from further rotation in the clamp set.

As shown in FIG. 1, the clamp set 100 also includes a pair of notches 172 located on the superior and inferior edges of the transverse plate 102. Notch 172 is located proximate to the center region 108 of the transverse plate 100. Superior notch 172 and inferior notch (not shown) provide suitable grasping elements for the tool of FIG. 5. While grasping elements as shown include indentations, the function of serving as suitable grasping elements for a tool is also accomplished by having protrusions on the clamp set to match indentions in the tool. Any other suitable configuration or combination of male and female elements may be used.

Figure 2:
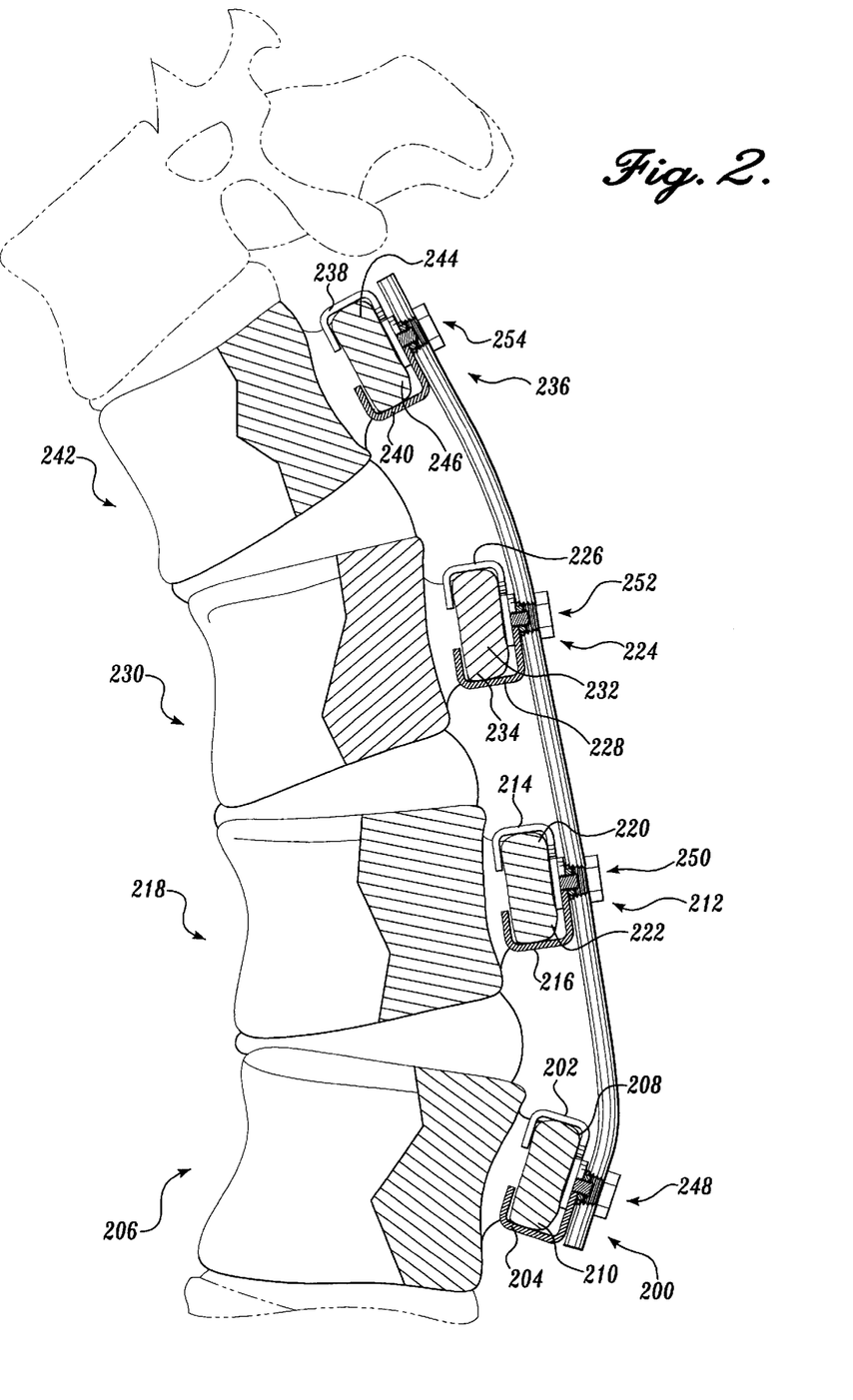
FIG. 2 shows a plan side view of an embodiment of FIG. 1 being used in an apparatus constructed in accordance with the present invention.

Referring now to FIG. 2, a preferred embodiment of the apparatus incorporating the clamp set of the present invention is shown. A portion of the thoracic region of the vertebral column having kyphotic curvature is shown with the apparatus affixed to four levels of thoracic vertebrae after reduction of the vertebral column has occurred. The preferred embodiment includes four clamp sets and a rail. While the apparatus as shown is affixed to adjacent vertebrae, most preferably, the clamp sets are affixed to alternate levels. For instance, a typical deformity is known as a right thoracic curvature, for this case, the four clamp sets would attach to the fourth, sixth, tenth and twelfth vertebra, preferably skipping the apical vertebra. At least two clamps are used in cooperation with a longitudinal rod, and at most seventeen, depending on the severity of the deformity. A single clamp set may be used without the longitudinal rail. Still another alternate is the use of a clamp set with only a single vertebral device.

A first clamp set 200 for use in the embodiment of FIG. 2 may be either of the alternate embodiments of FIG. 1, 3 or 4. The clamp set 200 includes a first 202 and a second 204 laminar hook in opposing configuration so as to clamp to a first vertebra 206 on a first 208 and second 210 lamina, respectively, of the first vertebra 206. It should be readily understood that a vertebra of the thoracic region of the spinal column inherently possesses a first and a second lamina as well as a first and a second pedicle. The first 202 and second 204 laminar hooks attach to first 208 and second 210 laminae from a superior and inferior direction, respectively. As can be perceived from FIG. 2, first 202 and second 204 laminar hooks surround the respective laminae 208 and 210, from three sides. The first clamp set 200 is posteriorly positioned in relation to the first vertebra 206 such that rail coupling member 248 is likewise posteriorly positioned.

A second clamp set 212 of the instrumentation apparatus similarly includes a third 214 and a fourth 216 laminar hook in opposing configuration so as to clamp to a second vertebra 218 on a third 220 and a fourth 222 lamina, respectively, of the second vertebra 218. The third 214 and fourth 216 laminar hooks attach to third 220 and fourth 222 laminae from a superior and inferior direction, respectively. As can be perceived from FIG. 2, third 214 and fourth 216 laminar hooks surround the respective laminae 220 and 222 from three sides. The second clamp set 212 is posteriorly positioned in relation to the second vertebra 218 such that rail coupling member 250 is likewise posteriorly positioned.

A third clamp set 224 similarly includes a fifth 226 and a sixth 228 laminar hook in opposing configuration so as to clamp to a third vertebra 230 on a fifth 232 and a sixth 234 lamina, respectively, of the third vertebra 230. The fifth 226 and sixth 228 laminar hooks attach to fifth 232 and sixth 234 laminae from a superior and inferior direction, respectively. As can be perceived from FIG. 2, fifth 226 and 228 laminar hooks surround the respective laminae 232 and 234 from three sides. The third clamp set 224 is posteriorly positioned in relation to the third vertebra 230, such that rail coupling member 252 is likewise posteriorly positioned. A fourth clamp set 236 similarly includes a seventh 238 and an eighth 240 laminar hooks in opposing configuration so as to clamp to a fourth vertebra 242 on a seventh 244 and an eighth 246 lamina of the fourth vertebra 242. The seventh 238 and eighth 240 laminar hooks attach to a seventh 244 and an eighth 246 laminae from a superior and inferior direction, respectively. As can be perceived from FIG. 2, seventh 238 and eighth 240 laminar hooks surround the respective laminae 244 and 246 from three sides. The fourth clamp set 236 is posteriorly positioned in relation to the fourth vertebra 242, such that rail coupling member 254 is likewise posteriorly positioned. Second 204, fourth 216, sixth 228 and eighth 240 laminar hooks are adjustable so as to enable placement of each clamp set on the respective vertebrae. The adjustable hooks are held to the clamp set by a nut.

A longitudinal rail 256 contoured to the reduced configuration of the spine is attached to each of the respective clamp sets 200, 212, 224 and 236 at the rail coupling member 248, 250, 252 and 254. The rail 256 is held to the clamp sets by the use of a nut snugged against the rail 256 at each rail coupling member 248, 250, 252 and 254. Each coupling member projects posteriorly in a region formerly occupied by the spinous process such that the rail likewise occupies the region occupied by the spinous process. Only a single central rail is required in the instrumentation constructed in accordance with the present invention. In applying the apparatus as described above, it should be readily understood that several elements of the vertebral column may have to removed in order to place the clamp sets and rail in the appropriate position. Since the apparatus is located centrally on the spinal column, the paraspinal muscles are not interfered with.

Use of the apparatus in spinal reduction will now be described with reference to FIGS. 2 and 3. To begin placement of the instrumentation on the spinal column, the apparatus must be in a disassembled state. As mentioned earlier, the preferred embodiment of this medical instrumentation will include four clamp sets 200, 212, 224 and 236. However, any number of clamp sets may be used depending on the particular situation of the patient. Therefore, description of the use of one clamp set will suffice to describe the use of the remaining three. The first clamp set 200 will be attached to one level 206 of the vertebral column after the spinous process and other anatomical features of the vertebra have been modified or even removed to accommodate the clamp set. The first hook 202 of the first clamp set 200 is placed over the first lamina 208 from a superior direction. Referring to FIG. 3, the first hook 114 being integral with the transverse plate 102 also places the transverse plate 102 on the posterior portion of the vertebra. Placement of the clamp set 200 on the vertebra 206 also locates rail coupling member 248 in the posterior configuration. First 156 and second 158 pedicle extensions shown in FIG. 3 will be positioned on the first and second pedicles of the vertebra such that first 156 and second 158 pedicle extensions will lie opposite to each other and lateral to the center region of the clamp set.

Referring now to FIG. 2, second hook 204 is now placed on a second lamina 210 from an inferior direction, such that first 202 and second 204 hook are in opposing configuration and provide a claw-like hold on the vertebra 206. Referring now to FIG. 3, second hook 148 may either slide into position around bolt 136, or second hook notch 148 may slide into position from the top of the bolt 136. Second hook 204 is made adjustable or detachable to facilitate placement on the second lamina 210. Once second hook 204 is placed in position, nut 138 may be snugged against second hook 124 at first and second fingers 150 and 152 at this time or may be loosely threaded for snugging at a later time. In any event, nut 138 is preferably snugged prior to adjustment of vertebra. Placement of the second 212, third 224 and fourth 226 clamp sets may now proceed at this time in much the same manner as the first clamp set 200. It should be readily apparent that the order of placement of the clamp sets on the vertebrae is of no consequence to the functioning of the apparatus. The advantages of the clamp set and apparatus should now be evident. The opposing hook configuration of the present invention provides a more reliable method of fastening posterior instrumentation to the spinal column than previously applied methods. In addition, the first 156 and second 158 pedicle extensions extend to cover all or part of the pedicles to transmit force downward on the pedicle during rotation of the vertebra. It should be readily apparent that only one of the two pedicle extensions will see a transmittance of force to the pedicle during rotation in any one direction. The pedicle extensions provide pressure distribution over a portion of the pedicle, decreasing the stress on the laminar hook, thus stronger rotational forces may be applied without fear of damaging bone or nerve tissue.

Once each of the individual clamp sets has been attached to its respective vertebra, the superiormost 236 and inferiornmost 200 clamp sets are held in the neutral position, i.e., the vertebra attached to these two clamp sets are not typically adjusted in the sagittal or coronal planes, but can be rotated axially, then held in place while the remaining vertebrae are adjusted. These clamp sets prevent transferring a rotational force beyond the construct to the vertebrae that are not instrumented (a problem known as crankshaft phenomena). Once the superiormost and inferiormost clamp sets are held in place, reduction of the remaining vertebrae can take place. In one procedure, a reduction tool is used to adjust the vertebra to achieve a more normal spinal configuration. A preferred reduction tool to be used in accordance with the present invention has a first member with a handle portion, a nose portion, and a neck portion connecting the handle portion to the nose portion. A similar second member has a handle, neck, and nose portions. The first and second members a are connected at the neck portions. The reduction tool will be described below. Once reduction has been performed on an individual vertebra, or at any time thereafter, the reduction tool is held in place by the use of a robotic arm. The robotic arm clamps or grasps onto the reduction tool at a suitable location. In one example, the tool is provided with a tab onto which the robotic arm may attach. Use of the tool and robotic arm maintains the vertebra in the corrected state.

Once reduction of the indicated vertebrae has taken place, the length and contour of the longitudinal rail 256 can be determined. Previous methods relied on having the rail contoured before reduction had taken place, thus anticipating the amount of reduction that could be achieved. While this approach may have succeeded in a few instances, other times it was found that the rail was either too short or too long or the curvature of the rail was undercompensated or overcompensated. One advantage of the present invention is that it provides a more reliable method of achieving the proper length and shape and curvature of a rail because the rail is measured, cut, and contoured to the proper length and shape after reduction has taken place.

The proper length and accurately contoured longitudinal rail 256 can now be attached to each of the individual clamp sets 200, 212, 224 and 236 in their reduced or neutral states at the respective coupling members 248, 250, 252 and 254. The longitudinal rail 256 fits into the slot of the rail coupling members and is snugged loosely with a nut at each clamp set to prevent the rail from escaping the clamp set. Further, final adjustment of the clamp sets can take place because the slot allows rotation of the rail while inside the slot when the nut is loosely threaded. It is not necessary to use the longitudinal rail as a derotation device once it is set into the clamp sets because the deformities have already been reduced. Whereas in previous methods, reduction took place by rotating a rod. This is where the big leap in safety between the method of the present invention and previous methods is achieved. Once the adjustment of the clamp sets is complete, the nuts are snugged down on the rail to prevent rotation of the clamp sets. In the preferred embodiment, the rail 256 has multiple sides which engage a suitably configured portion of the coupling member slot surface, as shown in FIG. 4. The more sides the rail has, the finer the reduction adjustment that can be achieved. A multi-sided rail engages the corresponding sides of the slot surface much like a hexagonal nut engaged in a wrench, thus a multi-sided longitudinal rail prevents any rotational slippage of the clamp set which would cause the vertebra to slip back into its deformed state. This is the difference between the present invention and the two rod system. Two rods were previously required to act in unison to prevent rotation of the vertebra back to the deformed condition. With a multi-sided nail, the rotational forces are held in check by the interlocking surfaces of the rail and slot. The nut, in this case, simply prevents the longitudinal rail releasing from the clamp set entirely and may only minimally relied upon to prevent rotation of the clamp set relative to the rail. The longitudinal rail holds the clamp sets in their reduced state and in relation to each other, therefore the longitudinal rail must be of sturdy construction to resist bending by torsional forces.

Figure 5:
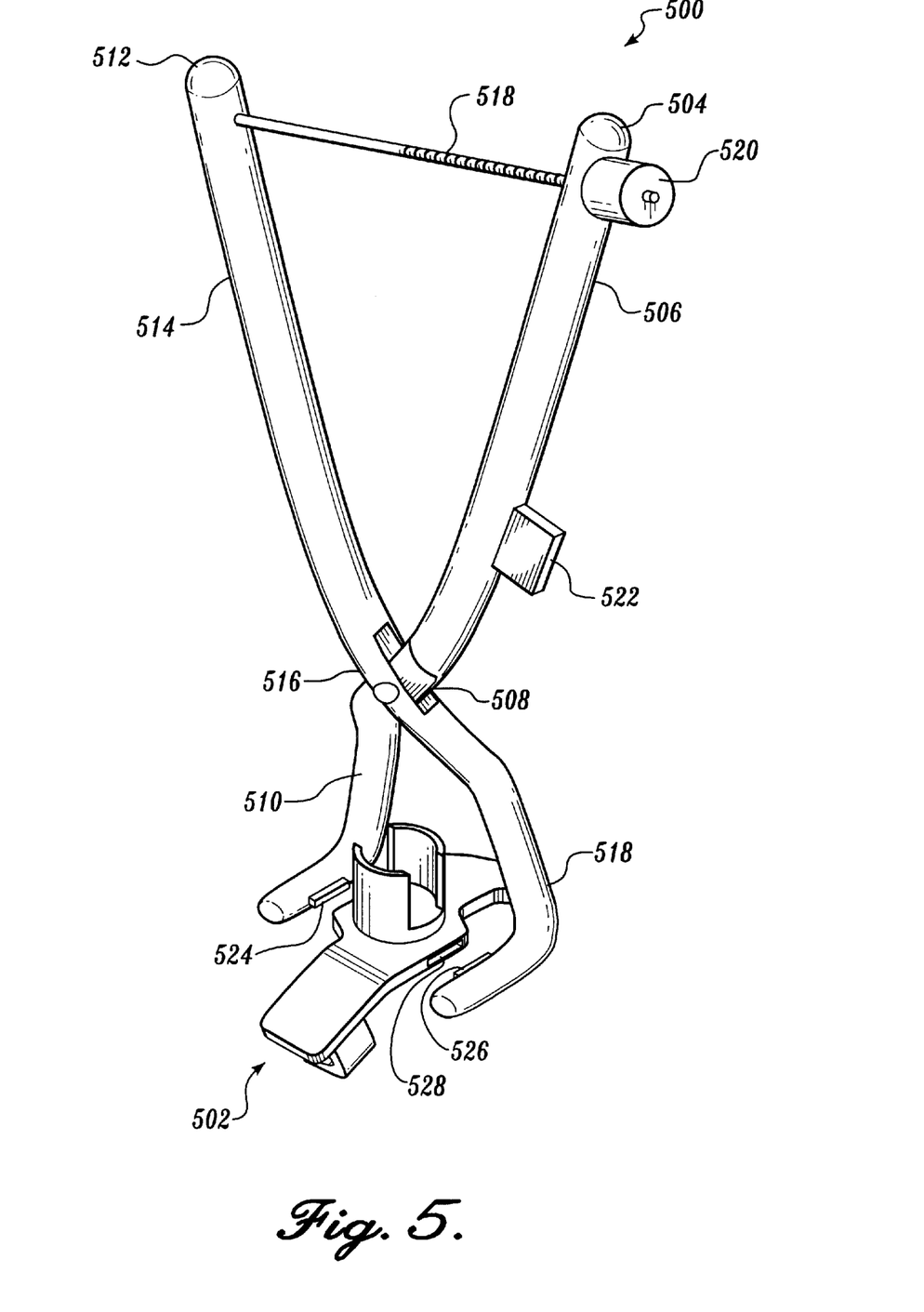
FIG. 5 shows a perspective view of a tool, constructed in accordance with the present invention.

In another aspect of the present invention, a tool is provided to use with the clamp set. FIG. 5 shows a tool 500 for adjusting an individual clamp set 502. The tool of the present invention includes a first arm member 504. The member 504 further includes a handle portion 506, a neck portion 508, and a nose portion 510. The tool also includes a second arm member 512. The second member also includes a handle portion 514, a neck portion 516, and a nose portion 518. The first arm member 504 and the second arm member 512 are pivotally connected at the neck portions 508 and 516. The elongated handle portions 506 and 514 allow for a multiplication of the gripping force at the relatively shorter nose portions 510 and 518. A threaded rod 518 is located proximate to the outermost ends of the handle portions 506 and 514. The rod 518 traverses one of the handle portions and is threaded to a securement nut 520 on the outside of the handle portion. Snugging on the nut 520 closes the handle portions 504 and 512 and applies the gripping force to the clamp set 502. The tool also includes a rectangular tab 522, for use during the spinal reduction method.

The nose portions 510 and 518 further include projections 524 and 526 on the inside surfaces facing the clamp set 502. The projections are suitably constructed so as to mate with the notches 528 on the traverse plate of the clamp set 502. Although projections on the nose portions have been described, the present invention can suitably also utilize indentations where the clamp set is provided with projections rather than notches. Further, any combination of mating parts may be utilized in the present invention.

Figure 6:
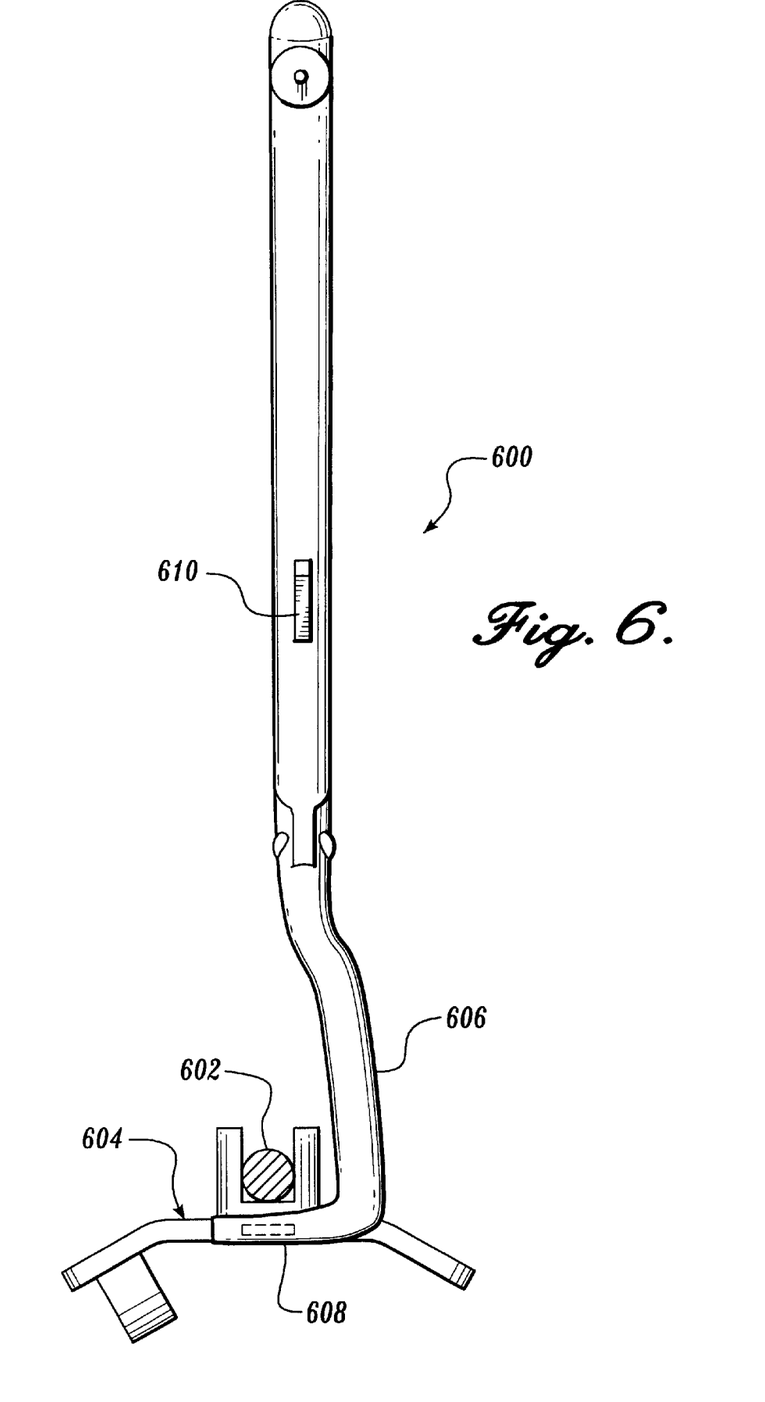
FIG. 6 shows a side plan view of the tool of FIG. 5.

Referring now to FIG. 6, a feature of the tool 600 according to the present invention is the ability to slide under the longitudinal rail 602 after the rail has been placed in the clamp set 604. As shown in FIG. 6, the nose portion 606 follows a curved line when viewed edgewise which takes the gripping end 608 of the nose portion 606 underneath the rail 602. In this manner, the tool 600 is first applied to the clamp set 604, the tool is then held at the tab 608 to a stabilizing arm (not shown). Next, the rail 602 is attached to the clamp set 604 and finally the tool 600 is removed.

Referring now to FIG. 7, another embodiment of the clamp set 700 according to the present invention includes pedicle screws 702 and 704 to use as securement devices rather than laminar hooks. Pedicle screws 702 and 704 traverse apertures 706 and 708 disposed in the body of the clamp set 700. Apertures 706 and 708 are countersunk so as to allow articulation of the pedicle screws 702 and 704 within the apertures. The clamp set 700 is meant to be similar in operation to the clamp sets shown in FIGS. 1, 3 and 4, in that the clamp set 700 has pedicle extensions to transmit downward rotational forces along the pedicle.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An apparatus for reducing spinal deformities, comprising:
   a plurality of vertebra clamp sets, wherein each set has a transverse plate with a center region and a first and a second end, the center region has a coupling member with a slot centered between the first and second ends and configured to receive rail and wherein each end has a surface with a plurality of curves configured to conform to the contours of the vertebra pedicle; and
   a rail which is coupled to each clamp set.

2. The apparatus of claim 1, wherein each of the clamp sets further comprises:
   a first laminar hook to hook on a superior portion of the first lamina, the first hook being located on the first end of the plate;
   a second laminar hook to hook on an inferior portion of the second lamina, the second hook being located on the second end of the plate, the first and second hook having a claw-like configuration, wherein at least one hook is adjustable; and
   a coupling member having a slot to receive a rail, the coupling member located on the center region of the plate and the slot being configured to the rail shape.

3. The apparatus of claim 2, wherein the rail shape is multi-sided.

4. The apparatus of claim 3, wherein the rail cross-sectional shape has any number of sides from 4 to 120.

5. The apparatus of claim 4, further comprising a second, third and fourth clamp set.

6. The apparatus of claim 1, wherein each clamp set further comprises angled plates from the center region to the ends and oppositely angled plates at the ends.

7. The apparatus of claim 1, wherein each clamp set further comprises notches at the center region, wherein said notches are configured to be grasped by a reduction tool.

8. A clamp set for affixing to a vertebra, comprising:
   a transverse plate with a center region and a first and a second end, wherein each end has a surface with a plurality of curves configured to conform to the contours of a vertebra pedicle; and
   a coupling member having a slot to receive a rail, the coupling member located on the center region of the plate and the slot being centered between the first and second ends and being configured to the rail shape.

9. The clamp set of claim 8, further comprising at least one vertebral securement device to secure the clamp set to a vertebra.

10. The clamp set of claim 9, further comprising:
    a first laminar hook to hook on a superior portion of a first lamina, the first hook being located on the first end of the plate; and
    a second laminar hook to hook on an inferior portion of a second lamina, the first and second laminae located on a vertebra, and the second hook being located on the second end of the plate, the first and second hook having a claw-like configuration, wherein at least one hook is adjustable.

11. The clamp set of claim 9, wherein the rail shape is multi-sided.

12. The clamp set of claim 11, wherein the rail shape has any number of sides from 4 to 120.

13. The clamp set of claim 8, further comprising angled plates from the center region to the ends and oppositely angled plates at the ends.

14. The clamp set of claim 8, further comprising notches at the center region, wherein said notches are configured to be grasped by a reduction tool.

15. An invasive method for reducing spinal deformities, comprising:
   (a) attaching a plurality of clamp sets to vertebra along a portion of the spine, wherein each clamp set has opposing pedicle extensions at its ends; and a slotted coupling member centered between the pedicle extensions and configured for receiving a rail.
   (b) adjusting the clamp sets to correct deformity, including rotating a vertebra by pushing on a pedicle with a pedicle extension end, wherein a majority of the surface of each pedicle extension is configured with a plurality of curves conforming to the contours of the pedicle;
   (c) holding the clamp sets in place; and
   (d) attaching a rail to the clamp sets, wherein the rail insubstantially induces further reduction of the deformity, and wherein the rail is centered between the pedicle extensions of each of the clamp sets.

16. The method of claim 15, further comprising the step of contouring the rail after the step of adjusting the clamp sets and before the step of attaching the rail to the clamp sets.

17. The method of claim 16, wherein the step of attaching a plurality of clamp sets further comprises:
   for clamp sets having a first and second laminar hook, hooking a first laminar hook on a first lamina, and hooking a second laminar hook on a second lamina, wherein the first and the second hook are in opposed configuration.

18. The method of claim 17, wherein the step of adjusting vertebrae, further comprises:
   for clamp sets having a pedicle extension, transmitting downward force on the pedicle during adjustment by use of the pedicle extension.

19. The method of claim 18, wherein the step of attaching a rail further comprises:
   holding the clamp sets in their adjusted states in relation to each other with the use of a multi-sided rail.

20. The method of claim 19, wherein the multi-sided rail has 4 to 120 sides.

21. The method of claim 20, wherein the portion of the spine is in the thoracic and lumbar region.

22. The method of claim 21, wherein the plurality of clamp sets is four.

23. The method of claim 15, further comprising the step of fixing the position of the clamp sets by use of a robotic arm after the step of adjusting the clamp sets.

* * * * *

UNITED STATES PATENT AND TRADEMARK OFFICE
CERTIFICATE OF CORRECTION

PATENT NO. : 6,458,131 B1 Page 1 of 1
DATED : October 1, 2002
INVENTOR(S) : R.C. Ray It is certified that error appears in the above-identified patent and that said Letters Patent is hereby corrected as shown below:

Column 12,
Line 16, "end, the" should read -- end, wherein the --.
Line 18, "receive rail" should read -- receive a rail --.

Column 13,
Line 18, "at its ends; and" should read -- at its ends, and --.
Line 20, "a rail." should read -- a rail; --.

Signed and Sealed this

Twentieth Day of September, 2005

JON W. DUDAS
*Director of the United States Patent and Trademark Office*